United States Patent [19]
Gleason et al.

[11] Patent Number: 4,552,893
[45] Date of Patent: Nov. 12, 1985

[54] LEUKOTRIENE ANTAGONISTS

[75] Inventors: John G. Gleason, Delran; Ralph F. Hall, Robbinsville, both of N.J.; Thomas W. Ku, Dresher, Pa.

[73] Assignee: SmithKline Beckman Corporation, Philadelphia, Pa.

[21] Appl. No.: 472,774

[22] Filed: Mar. 7, 1983

[51] Int. Cl.[4] .................. A61K 31/20; C07C 103/187; C07C 57/12; C07C 57/13
[52] U.S. Cl. .................... 514/560; 260/399; 260/402.5; 260/404; 260/404.5; 514/561; 514/564; 514/616; 514/626; 514/627; 562/556; 562/581; 564/154; 564/192
[58] Field of Search .................. 260/399, 402.5, 404, 260/404.5 R, 404.5 A; 424/318; 562/556, 581; 564/154, 192; 514/560, 561, 564, 616, 626, 627

[56] References Cited

U.S. PATENT DOCUMENTS

| | | | |
|---|---|---|---|
| 2,994,662 | 8/1961 | Calhoun et al. | 260/399 X |
| 4,061,634 | 12/1977 | Mod et al. | 260/402.5 X |
| 4,311,645 | 1/1982 | Rosenberger | 260/402.5 X |
| 4,461,775 | 7/1984 | Stanley et al. | 260/399 X |
| 4,469,705 | 9/1984 | Stanley et al. | 260/402.5 X |

FOREIGN PATENT DOCUMENTS 768907  2/1957  United Kingdom ............ 260/402.5

Primary Examiner—Thomas A. Waltz
Attorney, Agent, or Firm—Richard D. Foggio; Alan D. Lourie

[57] ABSTRACT

The compounds represented by the formula (I)

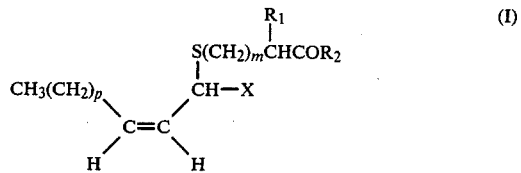

wherein m is 0, 1 or 2; p is 9, 10, 11, 12 or 13; $R_1$ is hydrogen, amino or

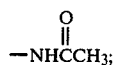
$-NHCCH_3$;

$R_2$ is hydroxyl, amino, $-NHCH_2CO_2H$,

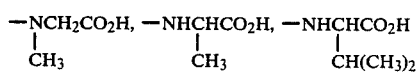

or $-NHCH_2CONH_2$; and X is $-CO_2H$, $-CH_2OH$ or

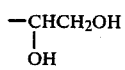

with the proviso that when m is 0, $R_1$ is hydrogen, or a pharmaceutically acceptable salt thereof have been found to be leukotriene antagonists and useful in the treatment of diseases in which leukotrienes are a factor, such as asthma.

15 Claims, No Drawings

LEUKOTRIENE ANTAGONISTS

BACKGROUND OF THE INVENTION

"Slow Reacting Substance of Anaphylaxis" (SRS-A) has been shown to be a highly potent broncho-constricting substance which is released primarily from mast cells and basophils on antigenic challenge. SRS-A has been proposed as a primary mediator in human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of cardiovascular effects of histamine.

The discovery of the naturally occurring leukotrienes and their relationship to SRS-A has reinforced interest in SRS-A and other arachidonate metabolites. SRS-A derived from mouse, rat, guinea pig and man have all been characterized as mixtures of leukotriene-$C_4$ ($LTC_4$), leukotriene-$D_4$ ($LTD_4$) and leukotriene-$E_4$ ($LTE_4$); the structural formulae of which are represented below.

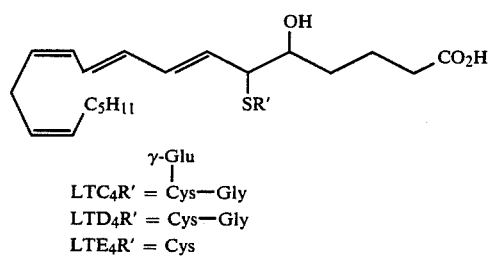

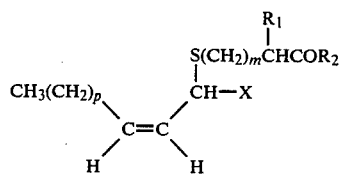

By antagonizing the effects of $LTC_4$, $LTD_4$ and $LTE_4$ or other pharmacologically active mediators at the end organ, airway smooth muscle, the compounds and pharmaceutical compositions of the instant invention are valuable in the treatment of diseases in which leukotrienes are a factor, such as asthma.

DETAILED DESCRIPTION OF THE INVENTION

The compounds of this invention are represented by the following general structural formula (I)

(I)

wherein m is 0, 1 or 2; p is 9, 10, 11, 12 or 13; $R_1$ is hydrogen, amino or

—NHCCH$_3$;
 ‖
 O $R_2$ is hydroxyl, amino, —NHCH$_2$CO$_2$H,

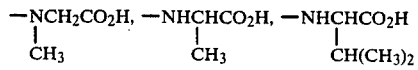

or —NHCH$_2$CONH$_2$; and X is —CO$_2$H, —CH$_2$OH or

—CHCH$_2$OH
 |
 OH with the proviso that when m is 0, $R_1$ is hydrogen, or a pharmaceutically acceptable salt thereof.

Illustrative of the compounds of formula (I) are those compounds in which the alkyl group adjacent to the double bond contains twelve carbon atoms (i.e. p is 11), which are represented by the general strucutral formula (II)

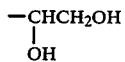

(II)

wherein m, $R_1$, $R_2$ and X are described above.

The compounds of formula (II) wherein X is —CO$_2$H are 3(Z)-hexadecenoic acid derivatives of formula (III)

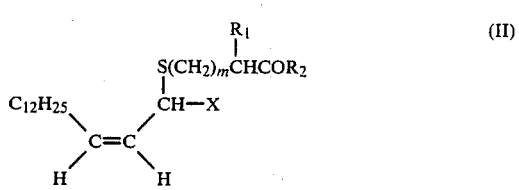

(III)

wherein m, $R_1$ and $R_2$ are described above. The 3(Z)-hexadecenoic acid derivatives of formula (III) are exemplified by 2-[(2-carboxyethyl)thio]-3(Z)-hexadecenoic acid, wherein m is 1, $R_1$ is hydrogen and $R_2$ is hydroxyl.

The compounds of formula (II) wherein X is —CH$_2$OH are 3(Z)-hexadecen-1-ol derivatives of the formula (IV)

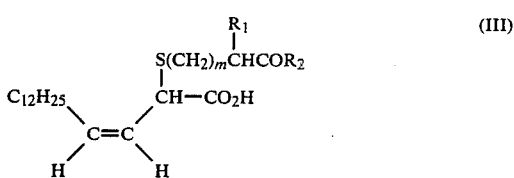

(IV)

wherein m, $R_1$ and $R_2$ are described above. The 3(Z)-hexadecen-1-ol derivatives of formula (IV) are exemplified by 2-[(2-carboxyethyl)thio]-3(Z)-hexadecen-1-ol, wherein m is 1, $R_1$ is hydrogen and $R_2$ is hydroxyl.

The compounds of the formula (II) wherein X is

—CHCH$_2$OH
 |
 OH are 4(Z)-heptadecen-1,2-diol derivatives of the formula (V)

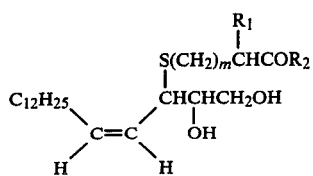

(V)

wherein m, $R_1$ and $R_2$ are described above. The 4(Z)-heptadecen-1,2-diol derivatives of formula (V) are exemplified by 3-[(2-carboxyethyl)thio]-4(Z)-heptadecen-1,2-diol, wherein m is 1, $R_1$ is hydrogen and $R_2$ is hydroxyl.

The compounds of formula (I) are prepared via the following synthetic pathways starting with 4-hydroxybut-2(E)-ene-1-al tetrahydropyranyl ether (1), wherein THP is a tetrahydropyranyl radical, as follows:

Pathway A

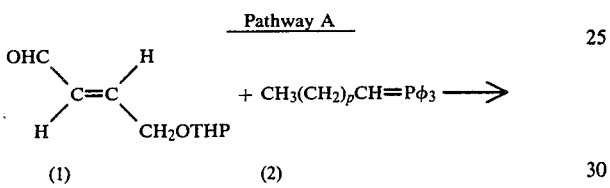

(1)   (2)

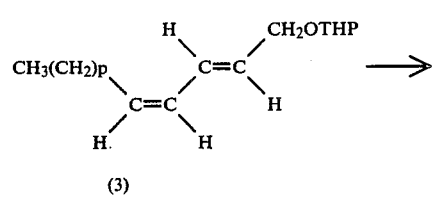

(3)

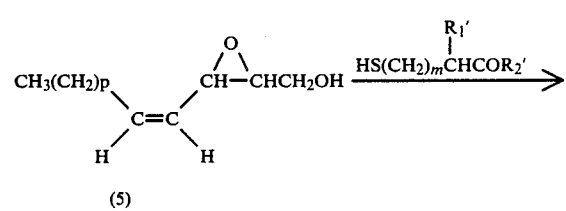

(4)

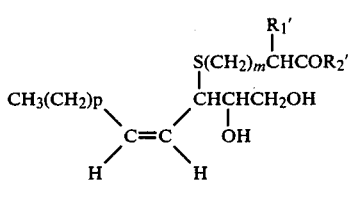

(5)

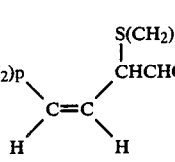

(6)

Pathway B

-continued

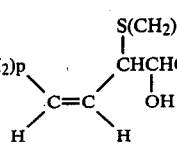

(6)

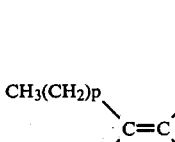

(7)

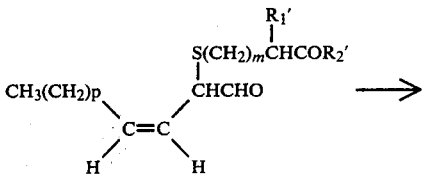

(8)

Pathway C

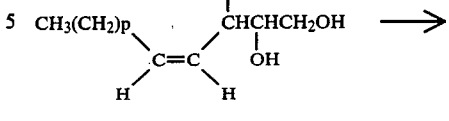

(7)

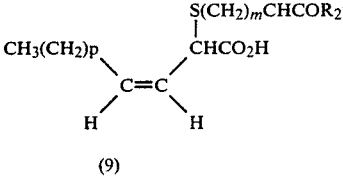

(9)

Compound (1), which is a known compound, is reacted with the appropriate alkyltriphenyl phosphonium ylid under Wittig conditions to yield compound (3). Compound (3) is hydroxyzed to cleave the THP ether and gives compound (4) which is epoxidized to afford compound (5). Compound (5) is reacted with the appropriate mercaptan, wherein $R_1'$ and $R_2'$ are $R_1$ and $R_2$ respectively as described above or a protecting radical which is easily converted into the desired substitutent, such as an alkyl ester or trifluoromethylacetamide, to give compound (6). Compound (6) may either (a) be easily converted into compounds of the formula (V) or analogs thereof; or (b) oxidatively cleaved to compound (7). Compound (7) may either (a) be reduced to compound (8) which is easily converted to compounds of the formula (IV) or analogs thereof or (b) oxidized to compound (9) which is easily converted into compounds of the formula (III) or analogs thereof.

The leukotriene antagonist activity of the compounds of this invention is measured by the ability of the compound to inhibit leukotriene induced contraction of guinea pig tracheal tissues in vitro. The following methodology was employed:

In vitro: Guinea pig (adult male albino Hartley strain) tracheal spiral strips of approximate dimensions 2 to 3 mm cross-sectional width and 3.5 cm length were bathed in modified Krebs buffer in jacketed 10 ml tissue bath and continously aerated with 95% $O_2$/5% $CO_2$. The tissues were connected via silk suture to force displacement transducers for recording isometric tension. The tissues were equilibrated for 1 hr., pretreated for 15 minutes with meclofenamic acid (1 $\mu$M) to remove intrinsic prostaglandin responses, and then pretreated for an additional 30 minutes with either the test compound or vehicle control. A cumulative concentration-response curve for $LTD_4$ on triplicate tissues was generated by successive increases in the bath concentration of the $LTD_4$. In order to minimize intertissue variability, the contractions elicited by $LTD_4$ were standardized as a percentage of the maximum response obtained to a reference agonist, carbachol (10 $\mu$M).

Calculations: The averages of the triplicate $LTD_4$ concentration-response curves both in the presence and absence of the test compound were plotted on log graph paper. The concentration of $LTD_4$ needed to elicit 30% of the contraction elicited by carbachol was measured and defined as the $EC_{30}$. The $pA_2$ value for the test compound was determined by the following equations:

1. $\dfrac{EC_{30} \text{ (presence of test compound)}}{EC_{30} \text{ (presence of vehicle control)}} = \text{dose ratio} = X$ 2. $K_B = \text{concentration of test compound}/(X-1)$ 3. $pA_2 \cong -\log K_B$ The compounds of this invention possess biosignificant antagonist activity against leukotrienes, primarily leukotriene $D_4$. Representative of the antagonist activity of the compounds of this invention, tabulated below are a number of claimed compounds and the $pA_2$ values calculated from the above test protocol.

| Compound | $pA_2$ |
| --- | --- |
| 2[(2-carboxyethyl)thio]-3(Z)-hexadecenoic acid | 6.0 |
| 2[(2-carboxyethyl)thio]-4(Z)-hexadecen-1-ol | 5.3 |
| 3[(2-carboxyethyl)thio]-4(Z)-heptadecen-1,2-diol | 5.2 |

The specificity of the antagonist activity of a number of the compounds of this invention is demonstrated by relatively low levels of antagonism toward agonists such as potassium chloride, carbachol, histamine and $PGF_{2\alpha}$.

Pharmaceutical compositions of the present invention comprise a pharmaceutical carrier or diluent and an amount of a compound of the formula (I) or a pharmaceutically acceptable salt, such as an alkali metal salt thereof sufficient to produce the inhibition of the effects of leukotrienes, such as symptoms of asthma and other allergic diseases.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier or diluent will, of course, depend upon the intended route of administration, i.e. parenterally or by inhalation.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant or compressed gas to be administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in less, equal or greater amounts than the solid active ingredient.

For parenteral administration the pharmaceutical composition will be in the form of a sterile injectable liquid such as an ampul or an aqueous or nonaqueous liquid suspension.

Usually a compound of formula I is administered to an animal subject in a composition comprising a nontoxic amount sufficient to produce an inhibition of the symptoms of an allergic response. When employed in this manner, the dosage of the composition is selected from the range of from 350 mg. to 700 mg. of active ingredient for each administration. For convenience, equal doses will be administered 1 to 4 times daily with the daily dosage regimen being selected from about 350 mg. to about 2800 mg.

The pharmaceutical preparations thus described are made following the conventional techniques of the pharmaceutical chemist as appropriate to the desired end product.

Included within the scope of this disclosure is the method of inhibiting the symptoms of an allergic response resulting from a mediator release which comprises administering to an animal subject a therapeutically effective amount for producing said inhibition of a compound of formula I, perferably in the form of a pharmaceutical composition. The administration may be carried out in dosage units at suitable intevals or in single doses as needed. Usually this method will be practiced when relief of allergic symptoms is specifically required, however, the method is also usefully carried out as continuous or prophylactic treatment. It is within the skill of the art to determine by routine experimentation the effective dosage to be administered from the dose range set forth above, taking into consideration such factors as the degree of severity of the allergic condition being treated, and so forth.

The following examples illustrate the preparation of the compounds of this invention and their incorporation into pharmaceutical compositions and as such are not to be considered as limiting the invention set forth in the claims appended hereto.

EXAMPLE 1

Preparation of 3-[(2-carboxyethyl)thio]-4(Z)-heptadecen-1,2-diol [Formula (V) wherein m is 1, $R_1$ is hydrogen and $R_2$ is hydroxyl].

(a) Heptadec-2(E),4(Z)-dienyl tetrahydropyranyl ether 1(a)(1)

Heptadec-2(E),4(E)-dienyl tetrahydropyranyl ether 1(a)(2)

Tridecyltriphenyl phosphonium bromide (189 g, 0.3 mole) was dissolved in 900 ml of tetrahydrofuran and cooled to 0° in an ice-salt bath while stirring under argon. A 2.2N solution of n-butyllithium in hexane (250 ml, 0.36 mole) was added dropwise over a period of 30 minutes. The mixture was stirred for an additional 20 minutes and then cooled to −70° in a dry ice-acetone bath. The 4-hydroxybut-2(E)-ene-1-al tetrahydropyranyl ether (51 g, 0.3 mole in 225 ml of tetrahydrofuran was added dropwise over a period of 35 minutes and the mixture stirred for an additional hour at −70°. The mixture was then poured into 6.25 liters of ether and stirred for 20 minutes. The resulting mixture was filtered through glass fiber filter paper. The filtrate was evaporated and the residue triturated with hexane, filtered and evaporated to give a ~3:1 mixture of 1(a)(1):-1(a)(2).

(b) Heptadec-2(E),4(Z)-dien-1-ol 1(b)(1)

Heptadec-2(E),4(E)-dien-1-ol 1(b)(2)

The mixture of compounds 1(a)(1) and 1(a)(2) (80 g, 0.24 mole) was dissolved in 3 liters of methanol and the pyridinine p-toluenesulfonic acid (3 g, 0.012 mole) was added to the mixture stirring under argon at room temperature. The progress at the reaction was monitored by tlc. When the reaction was complete the solvent was evaporated and the residue flash chromatographed on 500 grams of silica gel eluted with 10% ethyl acetate in hexane to give a ~3:1 mixture of 1(b)(1):1(b)(2). Separation of 1(b)(1) from 1(b)(2) was accomplished by careful chromatography on silica gel. Compound 1(b)(1) mp 34°-37°. Compound 1(b)(2) mp 51°-55°.

trans-2,3-epoxy-heptadec-4-Z-ene-1-ol 1(c)

Compound 1(b)(1) (2.52 g, 10 mmol) was dissolved in 100 ml of methylene chloride stirring at room temperature under argon. A 0.5N solution of sodium bicarbonate (30 ml) was added. The 85% m-chloroperbenzoic acid (2.03 g, 10 mmol) was added slowly in small portions. The mixture was stirred for 1.5 hours after the addition was complete. The phases were separated and the aqueous phase washed with methylene chloride. The combined organic phases were dried over anhydrous sodium sulfate filtered and evaporated. The residue was flash chromatographed on 100 grams of silica gel eluted with 10-20% ethyl acetate-hexane to give compound 1(c).

(d)
3-[(2-Carbomethoxyethyl)thio]-4(Z)-heptadecen-1,2-diol 1(d)

Compound 1(c) (7.2 g, 26.9 mmol) was dissolved in 40.2 ml of methanol containing 2% triethylamine. This solution was stirred at room temperature under argon and a solution of methyl-3-mercaptopropionate (4.92 ml, 44.4 mmol) and triethylamine (11.16 ml, 80.2 mmol) in 40.2 ml of methanol was added dropwise over a period of 15 minutes. The mixture was stirred for 5 hours at room temperature and then placed in the refrigerator overnight. The solvents were evaporated and the residue flash chromatographed on 500 grams of silica gel eluted with 10-15%, ethyl acetate in hexane to give compound 1(d), mp. 33°-36°.

(e) 3-[(2-Carboxyethyl)thio]-4(Z)-heptadecen-1,2-diol 1(e)

Compound 1(d) (500 mg, 1.29 mmol) was dissolved in 2 ml of methanol and stirred under argon. A 1N solution of sodium hydroxide (0.65 ml, 0.65 mmol) was added dropwise and the mixture stirred for 0.5 hours at room temperature. An addition of 0.65 ml of a 1N NaOH solution was added and the mixture stirred for 1 hour. TLC indicated that some starting material still remained so an additional 0.2 ml of a 1N NaOH solution was added and the mixture stirred for an additional 1.5 hours. The methanol was stripped off and the residue acidified with dilute hydrochloric acid. The mixture was extracted with diethyl ether and the organic phase dried with anhydrous magnesium sulfate, filtered, and evaporated to give crude product. This was recrystallized from diethyl ether-hexane to give the desired compound, mp 76°-77°.

|   | Theory | Found |
|---|--------|-------|
| C | 64.13  | 64.39 |
| H | 10.23  | 10.22 |
| S | 8.56   | 8.78  |

The following compounds are prepared by the general method of Example 1 by employing the appropriate thiol containing compound for methyl-3-mercaptoprionate:

3-[(carboxymethyl)thio]-4(Z)-heptadecen-1,2-diol;
3-[(3-carboxypropyl)thio]-4(Z)-heptadecen-1,2-diol;
3-[(3-carboxymethylamino-3-oxopropyl)thio]-4(Z)-heptadecen-1,2-diol;
3-[(2-amino-3-carboxymethylamino-3-oxopropyl)thio]-4(Z)-heptadecen-1,2-diol;
3-[[(aminocarbonyl)ethyl]thio]-4(Z)-heptadecen-1,2-diol; and
3-[(2-amino-2-carboxyethyl)thio]-4(Z)-heptadecen-1,2-diol.

EXAMPLE 2

Preparation of 2-[(2-carboxyethyl)thio]-3(Z)-hexadecen-1-ol [Formula (IV) wherein m is 1, $R_1$ is hydrogen and $R_2$ is hydroxyl].

(a) 2-[(2-Carbomethoxyethyl)thio]-3(Z)-hexadecen-1-al 2(a)

Compound 1(d) (2 g, 5.15 mmol) was dissolved in 10 ml of diethyl ether and stirred in a room temperature water bath. A saturated solution (100 ml) of periodic acid in diethyl ether was added in a single portion. The resulting mixture was stirred for two minutes and then immediately flash chromatographed on 150 g of silica gel with 10% ethylacetate in hexane to give compound 2(a).

(b) 2-[(2-Carbomethoxyethyl)thio]-3(Z)-hexadecen-1-ol

Compound from Example 2(a) (192 mg, 0.5 mmol) was dissolved in 1 ml of methanol and stirred at 0° under argon. Sodium borohydride (38 mg, 1 mmol) was added and the mixture stirred at 0° for 5 minutes. The mixture was acidified with dilute hydrochloric acid and evaporated. The residue was taken up in diethyl ether and washed with dilute hydrochloric acid, aqueous sodium bicarbonate, dried over anhydrous sodium sulfate, filtered and evaporated to give crude product which was flash chromatographed on 20 grams of silica gel eluted with 15% ethylacetate in hexane to give the above-noted compound.

(c) 2-[(2-Carboxyethyl)thio]-3(Z)-hexadecen-1-ol

Compound from Example 2(b) (180 mg, 0.5 mmol) was dissolved in 1 ml of methanol and a 1N solution of sodium hydroxide (1 ml, 1 mmol) was added. The mixture was stirred at room temperature under argon for 3 hours and then placed in the freezer over the weekend after which time it was stirred for an additional 2 hours at room temperature until tlc indicated only a trace of starting material remained. The methanol was stripped off and the residue acidified with dilute hydrochloric acid and extracted with chloroform. The organic phase dried over anhydrous magnesium sulfate filtered and evaporated to give crude product. This was recrystalized from hexane at −78° C. to give the desired compound, mp 39°–40°.

|   | Theory | Found |
|---|--------|-------|
| C | 66.23  | 66.47 |
| H | 10.53  | 10.77 |
| S | 9.30   | 9.15  |

The following compounds are prepared by the general method of Example 2 by employing the appropriate thiol containing compound for methyl-3-mercaptopropionate:

2-[(carboxymethyl)thio]-3(Z)-hexadecen-1-ol;
2-[(3-carboxypropyl)thio]-3(Z)-hexadecen-1-ol;
2-[(3-carboxymethylamino-3-oxopropyl)thio]-3(Z)-hexadecen-1-ol;
2-[(2-amino-3-carboxymethylamino-3-oxopropyl)thio]-3(Z)-hexadecen-1-ol;
2-[[(aminocarbonyl)ethyl]thio]-3(Z)-hexadecen-1-ol; and
2-[(2-amino-2-carboxyethyl)thio]-3(Z)-hexadecen-1-ol.

EXAMPLE 3

Preparation of 2-[(2-carboxyethyl)thio]-3(Z)-hexadecenoic acid [Formula (III) wherein m is 1, $R_1$ is hydrogen and $R_2$ is hydroxyl].

(a) 2-[(2-Carbomethoxyethyl)thio]-3(Z)-hexadecenoic acid 3(a)(1)

Methyl-2-[(2-carbomethoxyethyl)thio]-3(Z)-hexadecenoate 3(a)(2)

Compound from Example 2(a) (0.8 g, 2.25 mmol) was dissolved in 5.5 ml of acetone. The solution was cooled to −40° C. and stirred under argon Jones reagent (0.3 ml, 0.6 mmol) was added and the mixture stirred between −30° and −40° C. for 30 minutes. Additional Jones reagent (0.3 ml, 0.6 mmol) was added and the mixture stirred for 1 hour. The remaining Jones reagent (0.145 ml, 0.29 mmol) was added. Thirty minutes later the reaction which had been maintained in a temperature range of −30° to −40° C. throughout the reaction was quenched by the addition of 1 ml of isopropanol. The solvents were stripped off and the residue partitioned between diethyl ether and H₂O. The aqueous phase was extracted with diethyl ether. The combined organic phases were dried over anhydrous MgSO₄ filtered and evaporated to give the crude product 3(a)(1). In order to facilitate purification, compound 3(a)(1) was treated with excess diazomethane in diethyl ether at 0° and allowed to warm to room temperature. The solvents were evaporated and the residue flash chromatographed on 200 grams of silica gel eluted with 5% EtOAc-hexane to give the desired product 3(a)(2).

(b) 2-[(2-Carboxyethyl)thio]-3(Z)-hexadecenoic acid

Compound 3(a)(2) (0.16 g, 0.41 mmol) was dissolved in 3.2 ml of methanol and stirred under argon at 0° C. A 1N solution of sodium hydroxide (1.6 ml, 1.6 mmol) was added and the ice bath removed. The mixture was stirred at room temperature for 2½ hours. The methanol was evaporated and the residue cooled in an ice bath and acidified with dilute HCl. The aqueous phase was extracted twice with diethyl ether. The combined ether extracts were dried over anhydrous sodium sulfate, filtered and evaporated to give crude product. This was recrystallized from diethyl ether-hexane to give the desired compound, mp 52°–54° C. Anal. Calcd. C: 63.65; H: 9.56; S: 8.94; Found C: 63.59; H: 9.45; S: 9.24.

The following compounds are prepared by the general method of Example 3 by employing the appropriate thiol containing compound for methyl-3-mercaptoprionate:

2-[(carboxymethyl)thio]-3(Z)-hexadecenoic acid;
2-[(3-carboxypropyl)thio]-3(Z)-hexadecenoic adid;
2-[(3-carboxymethylamino-3-oxopropyl)thio]-3(Z)-hexadecenoic acid;
2-[(2-amino-3-carboxymethylamino-3-oxopropyl)thio]-3(Z)-hexadecenoic acid;
2-[[(aminocarbonyl)ethyl]thio]-3(Z)-hexadecenoic acid; and
2-[(2-amino-2-carboxyethyl)thio]-3(Z)-hexadecenoic acid.

EXAMPLE 4

As a specific embodiment of a composition of this invention, an active ingredient, such as the compound of Example 1(e), is dissolved in sterile water at a concentration of 0.5 percent and aerosolized from a nebulizer operating at an air flow adjusted to deliver the desired aerosolized weight of drug.

What is claimed is:

1. A compound represented by the structural formula (I)

$$CH_3(CH_2)_p \underset{H}{\overset{}{\diagdown}} C=C \underset{H}{\overset{CH-X}{\diagup}} \quad \begin{array}{c} R_1 \\ | \\ S(CH_2)_m CHCOR_2 \end{array}$$

wherein m is 0, 1 or 2; p is 9, 10, 11, 12 or 13; $R_1$ is hydrogen, amino or $$-NH\overset{\overset{O}{\|}}{C}CH_3;$$

$R_2$ is hydroxyl, amino, $-NHCH_2CO_2H$, $$-NCH_2CO_2H, \quad -NHCHCO_2H, \quad -NHCHCO_2H$$
$$\;\;\;|\qquad\qquad\quad\;\;|\qquad\qquad\qquad\;\;|$$
$$\;\;CH_3\qquad\qquad CH_3\qquad\qquad CH(CH_3)_2$$

or $-NHCH_2CONH_2$; and X is $-CO_2H$, $-CH_2OH$ or $$-CHCH_2OH$$
$$\;\;|$$
$$\;\;OH$$

with the proviso that when m is 0, $R_1$ is hydrogen, or a pharmaceutically acceptable salt thereof.

2. A compound according to claim 1 wherein X is $-CO_2H$.

3. A compound according to claim 2 wherein p is 11.

4. A compound according to claim 3 wherein m is 1, $R_1$ is hydrogen and $R_2$ is hydroxyl, designated 2-[(2-carboxyethyl)thio]-3(Z)-hexadecenoic acid.

5. A compound according to claim 1 wherein X is $-CH_2OH$.

6. A compound according to claim 5 wherein p is 11.

7. A compound according to claim 6 wherein m is 1, $R_1$ is hydrogen and $R_2$ is hydroxyl, designated 2-[(2-carboxyethyl)thio]-3(Z)-hexadecen-1-ol.

8. A compound according to claim 1 wherein X is $$-CHCH_2OH.$$
$$\;\;|$$
$$\;\;OH$$

9. A compound according to claim 8 wherein p is 11.

10. A compound according to claim 9 wherein m is 1, $R_1$ is hydrogen and $R_2$ is hydroxyl, designated 3-[(2-carboxyethyl)thio]-4(Z)-heptadecen-1,2-diol.

11. A pharmaceutical composition for inhibiting the effects of leukotriene in subjects in need of such inhibition comprising a pharmaceutical carrier or diluent and a nontoxic amount sufficient to produce said inhibition of a compound of claim 1.

12. A pharmaceutical composition according to claim 11 in a form suitable for administration by inhalation.

13. A pharmaceutical composition according to claim 12 in the form of an aerosol formulation.

14. A pharmaceutical composition according to claim 11 in a form suitable for administration by parenteral administration.

15. A pharmaceutical composition according to claim 14 in the form of a sterile solution.

* * * * *